United States Patent [19]

Ziegler et al.

[11] Patent Number: 5,064,059

[45] Date of Patent: Nov. 12, 1991

[54] DUAL CONTAINER SYSTEM WITH EXTRACTOR FOR STOPPER

[75] Inventors: John S. Ziegler, Arlington Heights; Sheldon M. Wecker, Libertyville, both of Ill.

[73] Assignee: Abbott Laboratories, Abbott Park, Ill.

[21] Appl. No.: 650,518

[22] Filed: Feb. 5, 1991

[51] Int. Cl.[5] ........................ B65D 51/00; A61M 5/14

[52] U.S. Cl. .................................... 206/221; 215/356; 215/364; 215/DIG. 8; 604/410; 604/416

[58] Field of Search ................ 206/221; 215/356, 364, 215/DIG. 8; 604/410, 416

[56] References Cited

U.S. PATENT DOCUMENTS

| | | | |
|---|---|---|---|
| 2,536,426 | 1/1951 | Oliveira | 215/364 X |
| 3,323,874 | 6/1967 | Phillips | 215/364 X |
| 4,614,267 | 9/1986 | Larkin | 206/221 |
| 4,614,515 | 9/1986 | Tripp et al. | 604/416 X |
| 4,784,259 | 11/1988 | Grabenkort | 215/354 X |
| 4,784,658 | 11/1988 | Grabenkort | 604/416 X |
| 4,865,189 | 9/1989 | Guerra et al. | 206/221 |
| 4,936,445 | 6/1990 | Grabenkort | 604/410 |

*Primary Examiner*—William I. Price

*Attorney, Agent, or Firm*—A. Nicholas Trausch

[57] ABSTRACT

Container systems employing a diluent container having an extractor that is helically threaded and is used to engage a resilient undercut vial stopper of an additive container.

13 Claims, 4 Drawing Sheets

DUAL CONTAINER SYSTEM WITH EXTRACTOR FOR STOPPER

BACKGROUND OF THE INVENTION

This invention relates to a dual container system such as a medicament-containing vial and a fluid source such as a flexible diluent container having associated means to effect sterile intermixing of the contents of the two containers by external manipulation after the containers are joined. More particularly, the present invention relates to an improved extractor for the flexible diluent container for use with a resilient undercut stopper closing the vial or the like which enhances the mechanical interlock between the vial stopper of the additive container and the extractor of the flexible diluent container without increasing the force necessary to engage the two containers. Thus the present invention enhances the reliability of engagement and activation as well as performs satisfactorily with a wide variety of stopper materials of varying resilience.

In particular, this invention is for use in systems involving packaging of a medicament and a diluent in separate containers which may be connected to one another at the time of use for convenient, safe mixing of the medicament and diluent in a sterile environment. Such container systems are known in the art and currently are sold by Abbott Laboratories of North Chicago, Ill. under the trademark ADD-VANTAGE. A number of embodiments of such systems are disclosed in U.S. Pat. No. 4,614,267 to Larkin, U.S. Pat. No. 4,784,259 to Grabenkort, U.S. Pat. No. 4,614,515 to Tripp and Larkin, and U.S. Pat. No. 4,784,658 to Grabenkort, all of which are assigned to the assignee of this invention, and all of which disclosures are hereby incorporated by reference.

In the noted system the flexible diluent container includes a tubular port which provides a means for securing thereto a stoppered medicament vial as well as a stopper removal means. The stoppers each have an undercut or shouldered recess in their exposed end. Previously the stopper removal means was composed of a truncated cone or mushroom shaped engagement element or extractor having a smooth surface and which is attached to a removable cover that covers and seals the inner end of the port. As a stoppered vial is advanced into and engaged with the port, normally by threaded interengagement, the vial stopper advances onto the extractor. The extractor thereby engages the stopper to subsequently pull the stopper from the vial when the cover is pulled from the port.

A wide variety of materials of varying hardness or resilience are used to manufacture vial stoppers since governmental approval is required for the type of material to be used with a particular medicament. Stoppers made from softer materials are susceptible to being pushed into the medicament vial during engagement by the extractor. Alternatively the extractor may be pulled out of the stopper during attempted extraction. Stoppers made from harder materials are often more difficult to engage. Difficulty of engagement between the vial stopper and port plug and in insuring the subsequent withdrawal of the stopper also is due in part to the wide variety of physical constructions of the outer surface of the vial stoppers e.g., tapered or cylindrical. Of course, the axial insertion force must be less than the force which will remove the port plug from the port closing position.

It is highly desirable to provide a diluent container with a port plug which will provide high reliability of engagement into the stoppers of vials despite variations in materials and constructions of those stoppers, to avoid pushing the stoppers into the vials and assuring withdrawal of any stopper with the extractor, and which will avoid pushing the cover off of the inner end of the port.

An important feature of this invention is that the extractor member or port plug has a universal capability of functioning with vial stoppers made from a wide variety of materials and in a wide variety of constructions. It provides very high reliability of engagement between the port plug of the flexible diluent container and vial stopper of the additive medicament vial and of subsequent withdrawal of the stopper.

It is therefore an object and advantage of the present invention to afford a diluent container with a port plug which has the aforementioned and other capabilities.

SUMMARY OF THE INVENTION

This invention relates to container systems employing a new extractor for use with a resilient undercut stopper that closes the open end of a vial or the like.

This invention relates to diluent containers with an improved extractor so as to facilitate the intermating between the vial stopper of the additive container and the extractor of the flexible diluent container thus providing high reliability of engagement. This is accomplished by a helically threaded extractor configuration which mitigates the axial force transfer from the extractor to the stopper during interengagement while preserving or increasing the size of the engagement head and thus the amount of force which can be transmitted from the extractor to the stopper for removing the stopper. In this manner the port fluid seal and vial stopper seal are maintained while the additive vial is engaged into the port of the flexible diluent container and the vial stopper becomes reliably engaged to the extractor of the flexible diluent container. This, in turn, enables the user to manipulate the bag and pull the stopper from the attached vial by pulling the extractor inwardly off the port, thus resulting in the mixing of the contents of the two compartments through the port. Normally this involves dumping of the contents of the vial into the diluent in the bag.

In a first configuration of this invention the medicament vial typically is screwed into the port of the diluent container with the recess of the vial stopper fitting over an engagement portion of the extractor which is partially threaded. In doing so, the helical threads of the extractor engage the constricted opening of the stopper throat in a manner to enhance the axial mating engagement therebetween and reduce axial resistance to passage of the large plug head through the neck of the stopper recess. With the helical threads of the port head having a lead greater than the threads of the vial which engage the port, a positive axial drawing action may be obtained so as to induce or "pull" the engagement portion of the port plug into the recess of the stopper. Once the extractor is fully seated, the shoulder at the base of the threads of the extractor engages the inward side of the throat shoulder of the stopper thus providing good gripping on the extractor when the user wants to manipulate the bag and pull the extractor stopper combination. The projecting threads also may remain in engagement with the surrounding wall portions of the stopper or contribute to the engagement on the throat shoulder.

In a second configuration of this invention, the recess of the vial stopper is configured with threads complementary to the threads of the extractor so as to further reduce axial resistance to passage of the plug head into the stopper recess.

In a third configuration of this invention, the extractor is fully threaded so as to make manufacturing easier besides other advantages.

The present invention differs from previous threaded extractors or port plug heads in that the thread depth and pitch are maximized, allowing significant engagement in non-threaded as well as threaded stoppers. Further the thread diameter preferably is tapered, allowing the thread to start with little effort and then pulling itself into the recessed stopper. Finally the leading flank of the thread is relieved so as to reduce friction when the parts are joined together.

One advantage of the present invention is that the tapered, threaded extractor with a partial thread and a stem portion can be used with the current non-threaded stoppers to facilitate an eventual transition to threads on both parts.

Another advantage of the present invention is that the tapered, threaded extractor is constructed so as to form and not cut threads temporarily in the constricting opening of the current elastomeric stoppers, thus facilitating entry with little effort and allowing passage of larger extractor heads than could be pushed in axially. A larger extractor provides more pulling force and greater reliability for activation of the system.

The concaved leading flank and the narrow crest of the male thread on the extractor reduces sliding friction during entry into the stopper recess. Also the flat trailing flank of the threads applies the maximum extraction force to the stopper.

The lead or axial travel per revolution of the threads on the extractor head and in the threaded stopper is greater than that of the vial and vial port threads. This draws the extractor head and stopper together quickly, which ensures complete engagement and neutralizes any initial compression which may develop before the thread is engaged.

The engagement portion of the extractor is larger in the axial direction than the axial length of the undercut portion of the stopper recess. This stretches the stopper axially and constricts it radially when the plug head bottoms out in the stopper recess. Together with friction in the rotational direction, this tends to break any adhesion which may have developed between the stopper and vial, making the stopper subsequently easier to extract without compromising the seal.

The tapered shape of the extractor head makes the stopper tend toward the same outside taper when engaged, which also makes the stopper easier to extract.

When a threaded stopper is used with a partially threaded or fully threaded extractor, a greater extraction force can be generated.

The fully threaded extractor, without the stem, allows for simplification and greater fidelity in molding, since the extractor head can be fully formed in an unscrewing mold component. The stem of the partially threaded extractor can only be formed by mold components which slide sideways, which increases mold complexity and compromises the fidelity of the thread.

DESCRIPTION OF THE PREFERRED EMBODIMENT

Figure 1:
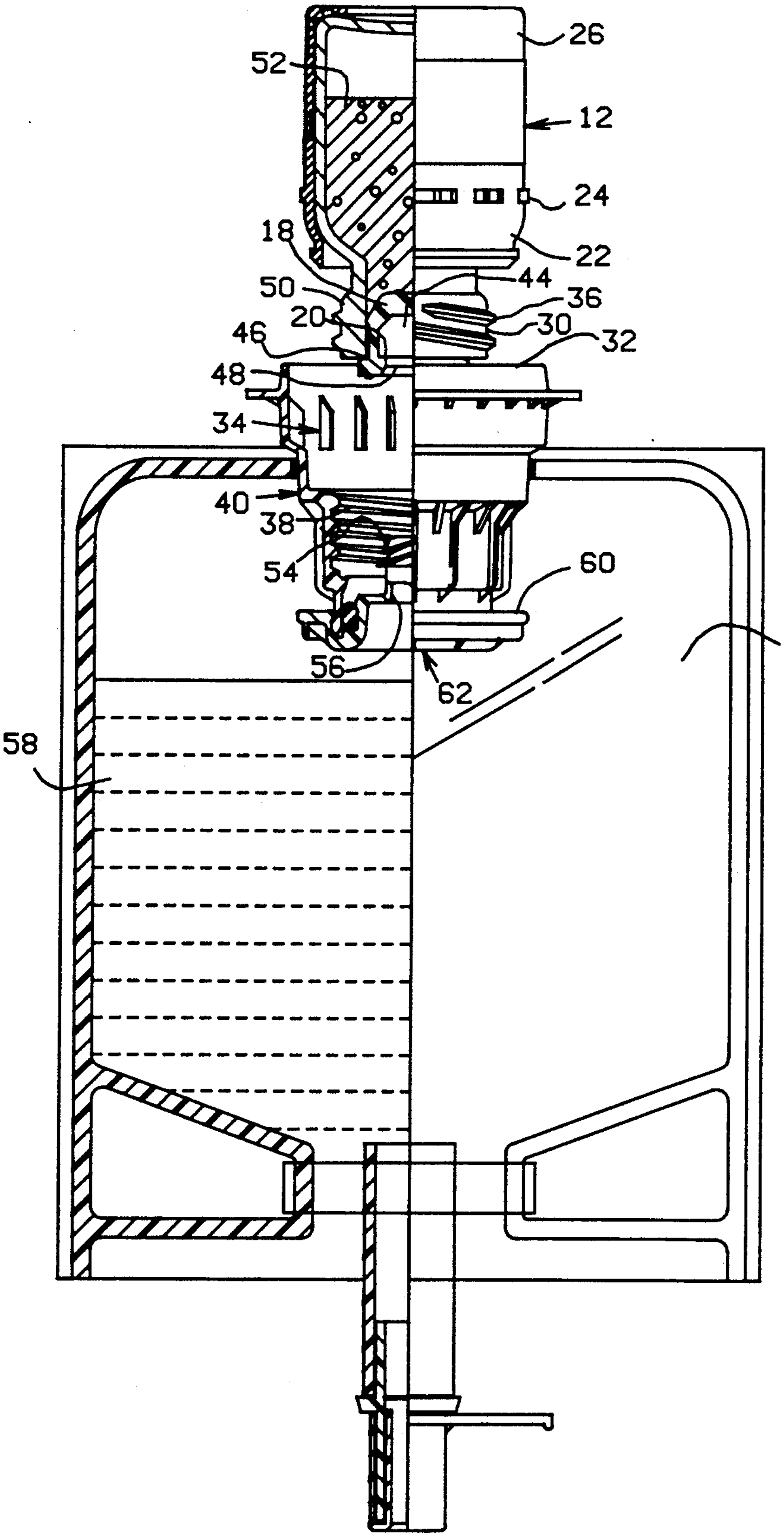
FIG. 1 is a front view, partially in section, of a flexible diluent container and an aligned additive medicament vial prior to engagement and constructed according to a preferred embodiment of the present invention.

Proceeding to a detailed description of the illustrated embodiment of the invention, FIG. 1 illustrates an additive medicament vial 12 just prior to being secured to the flexible diluent container 14. The diluent container typically is supplied with a protective cap over the outer end of the port. See for example the closure disclosed in U.S. Pat. No. 4,757,911 to Larkin, Tripp and Ziegler, and assigned to the assignee of this invention, the disclosure of which is hereby incorporated by reference. Such a closure is not shown in FIG. 1, it being assumed that the port has been opened by the health care technician in preparation for engagement of the vial. As previously indicated, the additive medicament vial will be supplied independently of the flexible container with the interconnection being effected, for example, by the health care technician. Typically the medicament vial is supplied with a stopper 18 in the vial opening 20 and a removable cap (not shown) covering the stopper for maintaining sterility as described in U.S. Pat. No. 4,614,515. The cap is detached from a skirt member 22 which is circumscribed by a ring of ratchet teeth 24. A shroud 26 covers the lower portion of the vial. A label overlaps the skirt and the shroud. The neck and discharge end portion 30 of the vial is exposed for engagement with the diluent container by tearing off the cap along an annular tear line, as described in U.S. Pat. No. 4,614,515. Once the caps are removed from the vial and from the outer end of the port, the vial may be inserted into the port 32 of the flexible container 14 with the ring of ratchet teeth 24 engaging complementary teeth 34 on the port to prevent easy removal of the vial.

Vial 12 has the usual end portion 30 with external threads 36 extending therefrom. Complementary port threads 38 extend internally from the port 32 which is mandrel sealed at 40 to the walls of the flexible container 14. The stopper 18 is formed with a undercut recess 44 with an annular lip or flange 46 defining an entrance opening 48 of reduced diameter and an annular internal shoulder 50 on its back or inward side defining the undercut recess portion.

When it is desired to mix the contents 52 of a vial 12 into a solution container 14, the caps are removed from the vial and from the outer end of the port, and the vial and solution container components are brought into mating alignment as in FIG. 1. Then the vial 12 is screwed into port 32 resulting in the recess 44 of the vial stopper 18 fitting over the engagement portion 54 of the port plug 56. The contents of the vial 12 and the contents 58 of the flexible container 14 may then be mixed by dumping the contents of vial 12 into the container 14, by removing the port plug-engaged stopper combination, 56 and 18. This is accomplished by manually pulling on the rim 60 of the cover portion 62 of the plug by manipulation from the exterior of the flexible bag 14, i.e., through the flexible container walls, as described further in the aforementioned patents.

Figure 2:
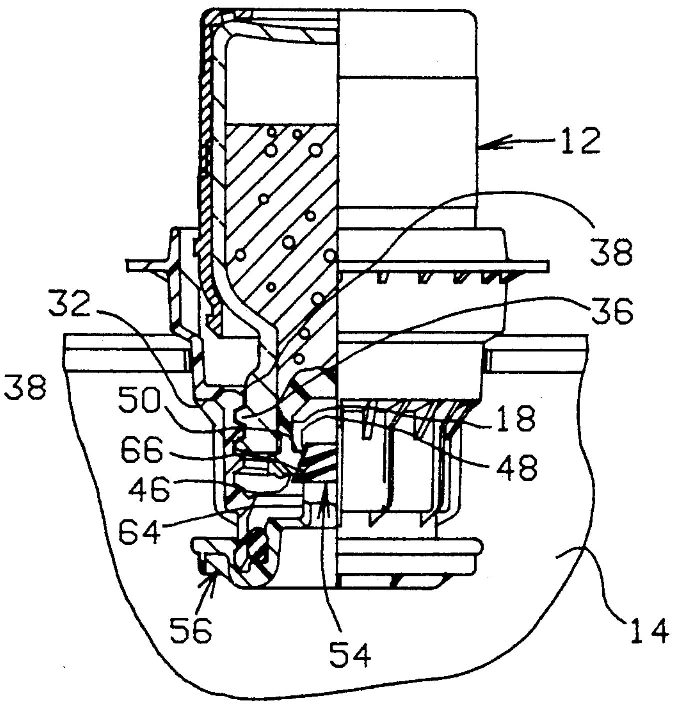
FIG. 2 is an enlarged partial view similar to FIG. 1 as the vial is being engaged with the flexible container.

FIG. 2 is an enlarged partial view of the engagement of the vial stopper 18 of the additive container and the extractor or port plug 56 of the flexible diluent container as the vial is being inserted into the port 32. The stopper 18 of the vial 12 is mated onto the engagement portion 54 of the port plug 56 as the vial is rotated and advanced in effecting the threaded engagement of the end of the vial 30 in the port 32 at threads 36 and 38. Helical threads 64 are provided on the extractor or plug head 66 to engage the stopper flange or lip 46 in the entrance opening 48 as the vial and its stopper are rotated, thereby to induce the axial engagement of the large plug head 66 into and through the smaller entrance opening 48 of the stopper recess. This reduces the axial forces that would otherwise be transmitted to the stopper when thrusting the plug head 66 through the entrance opening 48 of the stopper. Preferably this inducement to mating engagement between the plug head and the stopper is accomplished by the lead of the threads 64 being greater than the lead of the threads 36 and 38 of the vial and the port 32. This lead relationship tends to cause greater relative axial motion between the engagement portion of the extractor 56 and the stopper 18 than is occurring by virtue of the threading of the vial 12 into the port 32, thus tending to result in a drawing action between the port plug 56 and the stopper 18.

Figure 3:
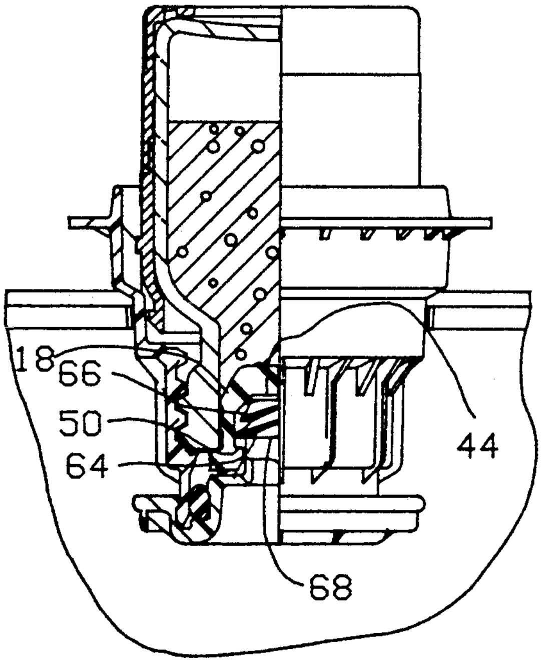
FIG. 3 is a view similar to FIG. 2 showing the vial fully engaged with the flexible container.

The stopper is rotated onto the head 66 as the vial is rotated into the threads 38 by virtue of the frictional engagement of the stopper 18 in the vial opening 20. This insertion step is illustrated in FIG. 2 where the leading edge of stopper 18 is inserted approximately halfway into port 32. Once the vial stopper is fully seated, as is shown in FIG. 3, the plug head 66 has fully entered recess 44. The proximal or undercut shoulder 68 on the engagement portion is disposed inward of the flange 46 and thus provides good interference gripping on the lateral shoulder 50 of the stopper when the user wants to manipulate the bag and pull the port plug-stopper combination from the seated, sealing position of FIG. 3. The extractor threads 64 further increase the effective width of the shoulder 68, and may continue to be in an engaging gripping relationship with the peripheral wall of the recess 36.

Figure 4:
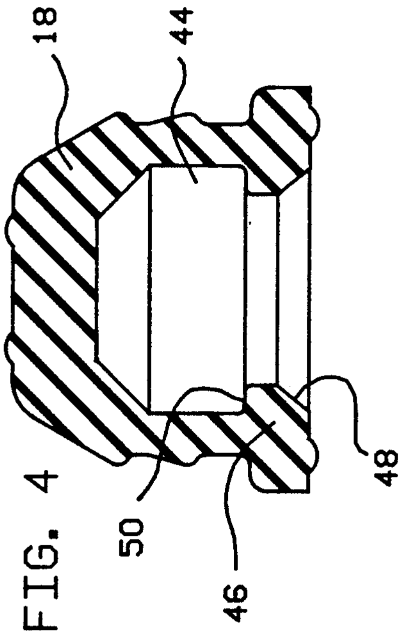
FIG. 4 is an enlarged view in section of the stopper shown in FIG. 1.
Figure 5:
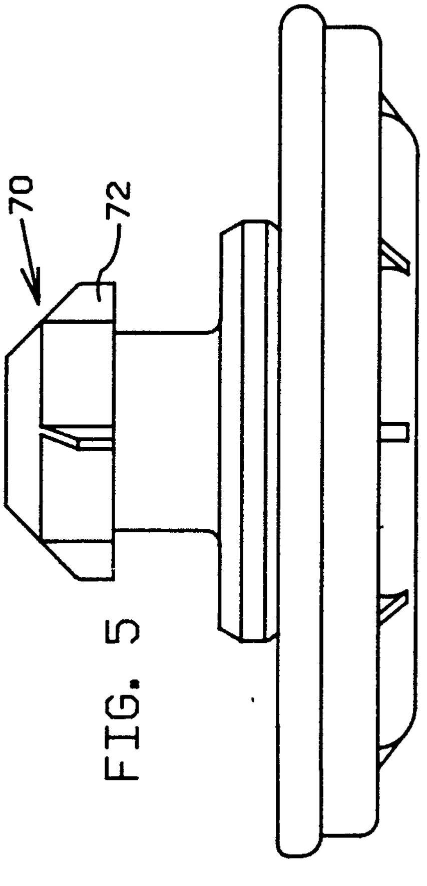
FIG. 5 is an enlarged side view of an extractor in current use with the stopper of FIG. 4.

FIG. 4 depicts a sectional view of the stopper having an undercut recess 44 currently in use. FIG. 5 depicts a vial port extractor plug 70 also currently in use. During engagement of the vial and the diluent container, the wings 72 of the plug 70 are axially forced into engagement with the stopper 18.

Figure 6:
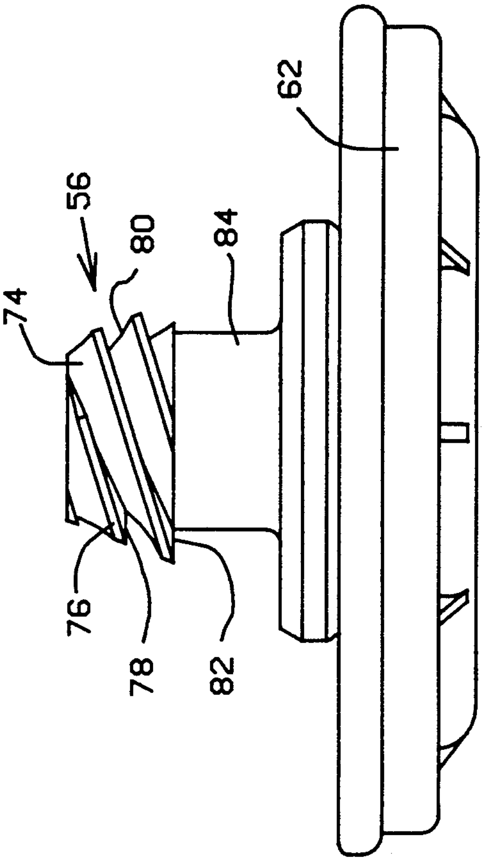
FIG. 6 is an enlarged view of the extractor depicted in FIG. 1 and showing a preferred embodiment having a partially threaded engaging portion according to the present invention.
Figure 7:
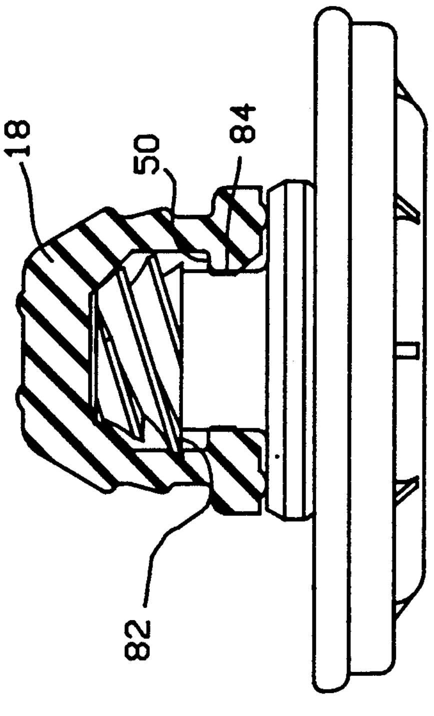
FIG. 7 is an enlarged view partially in section of the extractor of FIG. 6 engaged with the stopper of FIG. 4.

FIGS. 6 depicts a side view of a threaded extractor according to a preferred embodiment of the present invention. The extractor includes a engagement portion 74 which is preferably tapered. The engagement portion axially extends from the port internal cover 62 and includes helical threads 76. The threads have a flat trailing flank 78 for maximizing extraction force on the stopper. The relieved or concaved leading flank 80 and the narrow crest of the thread 76 reduce sliding friction during relative motion with the stopper. The diameter of the proximate (i.e. last) leading flank 82 is preferably equal to the diameter of the undercut recess portion of the stopper, as shown in FIG. 7. The extractor of FIG. 6 also includes a stem portion 84, the diameter of which is approximate the diameter of the stopper opening 48. The engagement portion of the extractor 74 and the stem portion 84 is larger in the axial direction than the axial length of the undercut recess 44 of the stopper. This stretches the stopper axially (as seen for example in FIG. 7) which tends to break any adhesion which may have developed between the stopper and vial, making the stopper easier to extract.

Figure 8:
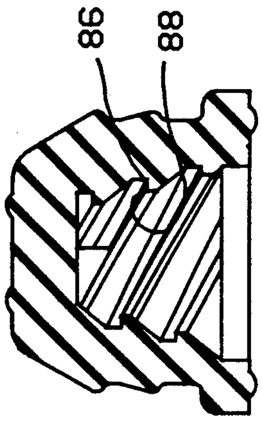
FIG. 8 is an enlarged view of an alternative stopper similar to FIG. 4 but having a threaded recess according to a further embodiment of the present invention.

FIG. 8 is an alternative stopper having a threaded recess. The root diameter 86 of the female thread is undercut relative to the crest diameter 88. The thread configuration is preferably tapered as shown, although a straight untapered thread will also engage with the male threads of the partial threaded extractor and stem of FIG. 7 or the fully threaded extractor of FIG. 9. A greater extraction force can be generated when a threaded stopper is used with a partially threaded or fully threaded extractor.

Figure 9:
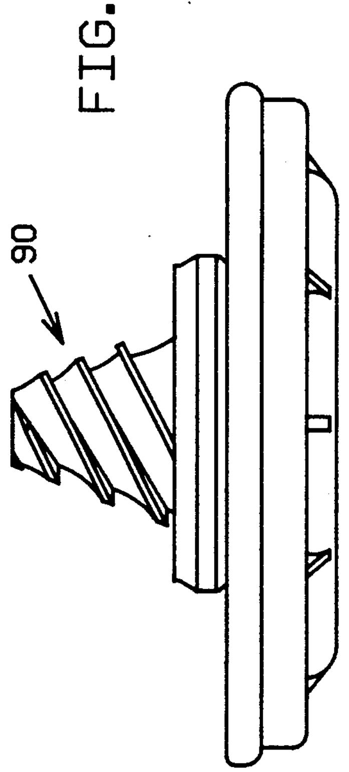
FIG. 9 is an enlarged view of an extractor similar to FIG. 6 but showing a fully threaded engaging portion according to a further embodiment of the present invention.

FIG. 9 depicts a fully threaded extractor without a stem that allows for simplification and greater fidelity in the molding process.

The engagement or extractor portion 74 of the extractor or port plug 56 in FIG. 6 for example is tapered from a minimum diameter smaller than the diameter of throat opening 48. When used with stopper 18, this construction facilitates and eases the movement of the head and threads 78 into and through the resilient opening 48 by pressing outward the engaged portion of lip 46. This enables engagement portion 74 to easily enter recess 44 of the vial stopper 18. As noted above, the helical threads 76 then act to facilitate and induce the movement of the tapered head 74 into the recess 44 as the vial is rotated and threaded into its seated position. The lead of threads 76 should be approximately equal to or greater than the lead of the vial and port threads 24 and 34 to avoid pushing the stopper away from the engaging head 74 and back into the vial. Preferably the lead of the threads 76 is substantial so as to gain a relative drawing action between the engagement portion 74 and the engaged portion of the stopper 18 as noted above. Such threading engagement is particularly advantageous when the stopper 18 is composed of relatively firm, less resilient materials. The outer diameter dimension across the last following or proximal edges 82 of the helical threads 76 is approximately equal to or slightly greater than the diameter at the shoulder 50 of the undercut portion of the recess 44 as seen in FIG. 7. The stem portion 84 is also undercut from the following edge 82 and has a diameter approximate the entrance opening 48 of the stopper 18.

FIG. 6 further illustrates the disposition of the helical threads 76 and the taper and relief affected at their leading flanks 80 to facilitate entry into the entrance opening 48. The threads also have a narrow crest, as best seen in FIG. 6. A number of parameters can be varied in regards to the construction of the port plug including the number of helical threads, their pitch, diameter and lead, and thus helical lead angle, and the diameter of the head 66 of the port plug itself.

A specific illustrative embodiment of a threaded port plug constructed according to the present invention is the three lead thread version as illustrated in FIGS. 6–9. Here the thread pitch is 0.105" and the lead is 0.315". The major outside diameter of the helical threads 64 starts at 0.402". Each trailing flank is flat and is in a plane normal to the helical axis. Such a head is used for engaging stoppers having a opening 48 about 0.282" in diameter, a undercut recess 44 about 0.362" in diameter and a lip flange about 0.100" thick in a vial having lead threads having a pitch of 0.125" and a lead of 0.250".

OPERATION

After the closure is removed from a diluent container 14 and the end cap is removed from a selected vial 12, the vial is ready to be inserted into the flexible container 14 as shown in FIG. 1. In this position the medicament vial 12 is ready to be screwed into the port 32. The interengagement of vial 12 and port 32 is accomplished by threadable engagement of threads 36 with complementary threads 38 within port 32. Rotating vial 12 with respect to the flexible container 14 causes end 30 to be drawn into port 32. This drawing action causes engagement portion 54 of the port plug 56 to enter the recess 44 in stopper 18 as well as effecting sealing engagement of the vial with the port. As the vial 12 is screwed into port 32 and stopper 18 is rotated by the vial, the threads 64 on the extractor or port plug 56 threadably engage the entrance opening of the stopper to induce engagement of the stopper onto the extractor and reduce the amount of axial insertion force otherwise imparted to the stopper. When engagement portion 54 has completely entered recess 44, the proximate flank 82 and the shoulder 50 fully and positively engage the stopper. The ratchet teeth 24 engage the compatible ratchet teeth 34 in the port thus preventing the vial 12 from being easily backed out of port 32 once interengagement has begun. When the port plug 56 is fully seated as is shown in FIG. 3, a great amount of force is required to disengage the port plug from the stopper 18. This ensures that the stopper 18 will be removed from the vial 12 when the extractor or port plug 56 is removed from the port 32 by manually manipulating the cover 62 from the exterior of the flexible container 14 without the stopper 18 and extractor 56 becoming disengaged from one another.

Such removal of the port plug 56 and stopper 18 combination will create an open path through vial opening 20 for medicament 52 to intermix with diluent 58. Diluent 58 and medicament 52 may be further intermixed by squeezing the sides of the flexible container 14. The preferred material for the port plug is a polypropylene copolymer.

The invention has been described as used in one particular system. Activation of the drug delivery system including the mixing of the medicament and diluent by removal of the port plug-stopper combination may be readily accomplished by health care or pharmacy personnel without the use of specially designed components or sophisticated methods which require an excessive number of procedures or prolonged exposure which might jeopardize sterility. It will be appreciated that the invention may be embodied in other similar systems.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. In combination, an extractor means for a flexible diluent container and a removable resilient stopper for closing a second engageable container;

said removable stopper having an undercut recess in an exposed end of said stopper, said undercut recess comprising an entrance opening having a first diameter and an undercut portion having a second larger diameter;

said extractor means including an engagement portion protruding along an axis for engaging said stopper within said undercut recess for removal of the stopper from said second container when said second container is engaged with said diluent container, said engagement portion comprising helical threaded means having tapering diametrical dimensions such that a leading end of said helical threaded means has a diameter less than the first diameter of said undercut recess and a following portion of said helical threaded means has a diameter at least approximately equal to the second diameter of said undercut recess.

2. The combination of claim 1 wherein said helical threaded means extends from the leading end of said engagement portion a predetermined length along the protruding axis.

3. The combination of claim 2 wherein the predetermined length of the helical threaded means is the entire length of the protruding axis.

4. The combination of claim 2 wherein said undercut portion of said stopper has a predetermined axial depth.

5. The combination of claim 4 wherein said predetermined length of said engagement portion is slightly greater than said predetermined axial depth of said undercut portion.

6. The combination of claim 1 wherein said undercut recess of said stopper has a threaded configuration and said entrance opening diameter is the crest diameter of the thread and said undercut portion diameter, is the root diameter of the thread.

7. The combination of claim 6 wherein said threaded configuration is tapered.

8. The combination of claim 7 wherein said helical threaded means extends from the leading end of said engagement portion a predetermined length along the protruding axis.

9. The combination of claim 8 wherein the predetermined length of the helical threaded means is the entire length of the protruding axis 10. The combination of claim 8 wherein said undercut portion of said stopper has a predetermined axial depth.

11. The combination of claim 10 wherein said predetermined length of said threads on said engagement portion is slightly greater than said predetermined axial depth.

12. An extractor means for a flexible diluent container including an access port having first means for engaging the removable resilient stopper having an undercut recess in an exposed end of said stopper, said undercut recess having an entrance opening having a first diameter and an undercut portion having a second diameter, said extractor means comprising an engagement portion extending along a first axis for engaging said stopper within said recess thereof, for removal of the stopper from such a second container when engaged with said first means, wherein said engagement portion comprises helical threaded means having tapering diametrical dimensions such that a leading end of said helical threaded means has a diameter less than the first diameter of said undercut recess and a following portion of said helical threaded means has a diameter at least approximately equal to the second diameter of the undercut recess.

13. A removable resilient stopper for closing a vial or the like having a threaded recess in an exposed end of said stopper wherein said threads are tapered.

* * * * *